United States Patent [19]

Linman et al.

[11] Patent Number: 5,733,401
[45] Date of Patent: Mar. 31, 1998

[54] CONTINUOUS, HIGH-SPEED METHOD FOR PRODUCING A PANT-STYLE GARMENT HAVING A PAIR OF ELASTICIZED LEG OPENINGS

[75] Inventors: E. Kelly Linman; Russell P. Bridges, both of Cincinnati, Ohio

[73] Assignee: The Procter & Gamble Company, Cincinnati, Ohio

[21] Appl. No.: 869,806

[22] Filed: Jun. 5, 1997

Related U.S. Application Data

[62] Division of Ser. No. 645,399, May 13, 1996.

[51] Int. Cl.$^6$ .................................................. A61F 13/15
[52] U.S. Cl. ...................... 156/160; 156/204; 156/229; 156/265; 156/290; 156/308.4
[58] Field of Search ........................ 156/73.1, 160, 156/199, 204, 229, 250, 251, 265, 267, 290, 308.4

[56] References Cited

U.S. PATENT DOCUMENTS

| | | | |
|---|---|---|---|
| 5,213,645 | 5/1993 | Nomura et al. | 156/164 |
| 5,393,360 | 2/1995 | Bridges et al. | 156/73.3 |
| 5,509,985 | 4/1996 | Kock | 156/160 |
| 5,516,392 | 5/1996 | Bridges et al. | 156/160 |
| 5,518,566 | 5/1996 | Bridges et al. | 156/161 |

*Primary Examiner*—James Sells
*Attorney, Agent, or Firm*—Theodore P. Cummings; Steven W. Miller; Jacobus C. Rasser

[57] ABSTRACT

A method for producing a pant-style garment from a substrate having a plurality of tensioned garters. A garter is any continuous loop of elastic material or a laminate of elastic bands and one or more flexible backing sheets. In one embodiment a substrate is joined to one or more mandrels having tensioned garters fired thereon. Substrate material is removed from within the loop of the garter, thereby forming apertures in the substrate. The substrate is folded along its longitudinal centerline such that its longitudinal edges meet. The substrate is subsequently joined along lines of joinder, and the substrate is cut into individual pant-style garments. In preferable embodiments, a process for providing elastics to the longitudinal edges of the substrate, thereby producing elasticized waistbands is included.

2 Claims, 7 Drawing Sheets

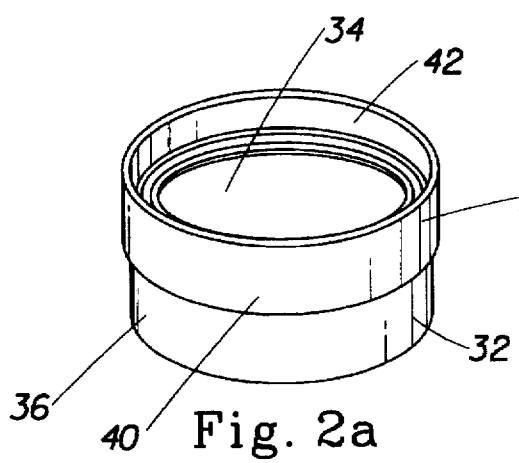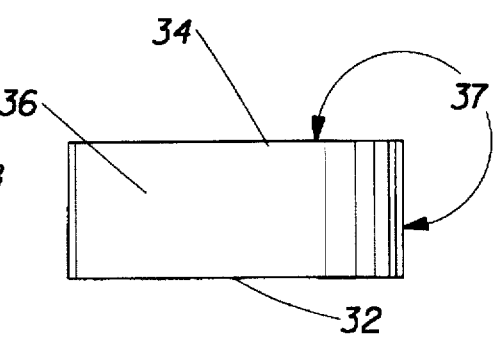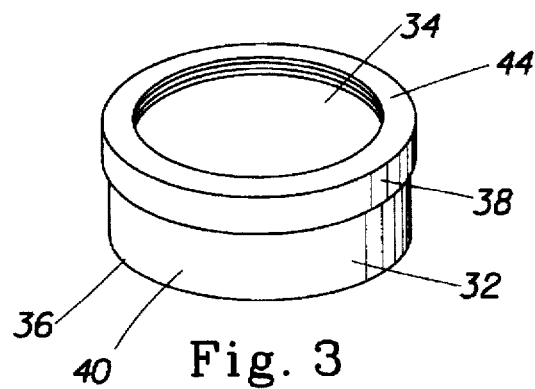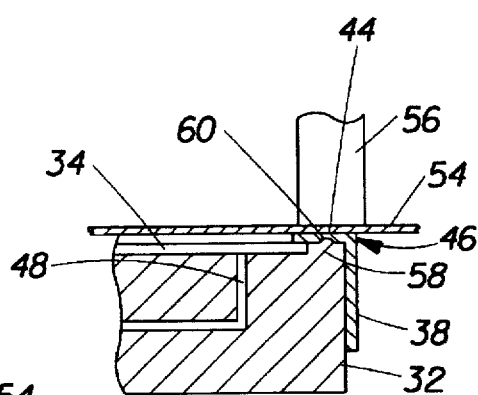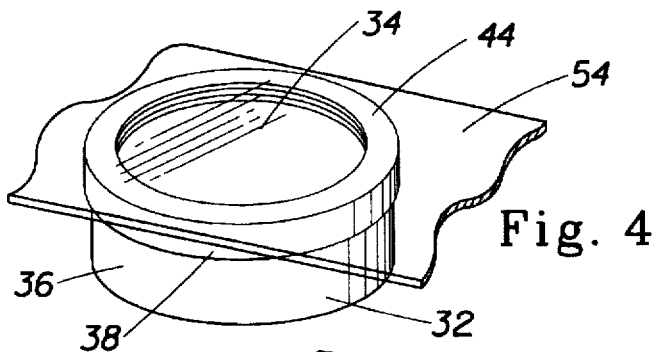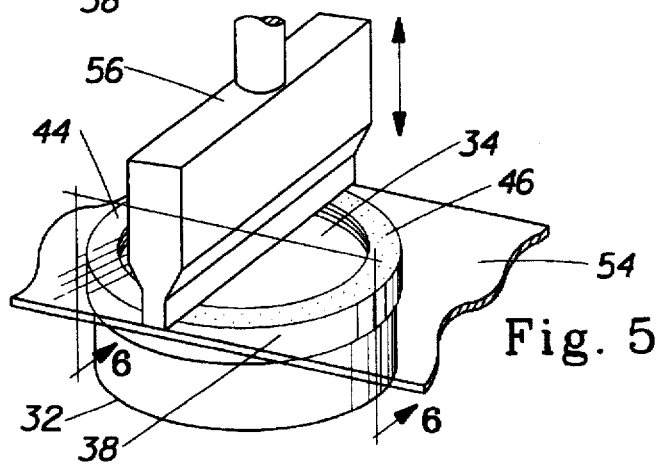

5,733,401

CONTINUOUS, HIGH-SPEED METHOD FOR PRODUCING A PANT-STYLE GARMENT HAVING A PAIR OF ELASTICIZED LEG OPENINGS

This is a division of application Ser. No. 08/645,399, filed on May 13, 1996.

FIELD OF THE INVENTION

The present invention relates to a process for creating pant-style garments by elasticizing an article by bonding a tensioned elastic member to it, more particularly, to a process wherein the elastic member is a garter stretched in more than one direction and the article is a substrate, and even more particularly, to a process wherein a tensioned elastic garter is held in a predetermined shape by a mandrel as it is bonded to a substrate. The substrate is then folded, joined at specific locations and cut to form individual pant-style garments in a high-speed, continuous process.

BACKGROUND OF THE INVENTION

Elasticizing a flexible substrate, such as a woven web, a nonwoven web, or plastic film, may be accomplished by attaching a tensioned elastic member to it. When the elastic member contracts, the flexible substrate wrinkles or shirrs to contract in dimension along with the elastic member. Subsequently, the substrate can stretch as though it were itself elastic. This concept is used, for example, in the manufacture of disposable diapers to provide elastic leg openings for snug, leak-resistant, body fit.

There are many commercial processes for combining elastic members with substrate materials. However, reliably combining tensioned elastics with a continuously moving substrate web, as is required in high speed diaper-making systems, has required relatively complex methods and apparatii.

If, for example, elasticity is needed only in the machine direction (the direction of travel of a continuously moving web), a continuous elastic ribbon may be fed parallel to the direction of substrate web travel from a source metering the elastic ribbon at a lower rate of speed than the speed of the substrate web. As the elastic ribbon is progressively bonded to the substrate web in the nip of a pair of sealing rolls, the elastic is stretched between its metering source and the sealing rolls. It is stretched an amount depending on the speed differential between the substrate web and the elastic ribbon metering rolls. This represents one of the simplest processes for combining elastics with moving webs.

Where tensioned elastics are applied in cross machine direction or at some other angle to machine direction, more complex systems have been required. For example, the substrate web may be passed through a festoon system whereby the continuously moving web is effectively indexed. That is, the substrate web is stopped for a short time along a portion of its path while the remainder of the web continues to move within a series of accumulation rolls. An elastic ribbon may then be sequentially stretched and bonded in any direction to the temporarily stationary portion of the web.

Where elasticity is desired in curved profiles, such as in elasticized diaper leg openings, even more complex processes have been required. For example, an elastic ribbon may be tensioned and then heat deactivated to cause it to become inelastic after it has been elongated. The inelastic ribbon may then be profiled, such as by camming the ribbon in a sinusoidal fashion perpendicular to machine direction as the ribbon is bonded to a substrate web. Because the elastic property is deactivated, the ribbon can be handled without concern for contraction forces disrupting the curved profile before and during bonding. Later, after the shaped elastic has been bonded to the substrate web, a separate heat reactivation step reestablishes the elasticity of the profiled ribbon. Because of the need for heat deactivation and reactivation, elastic material choices are limited. Such processes are complicated by the fact that whenever heat is applied to polymer elastic materials, the temperature must be accurately controlled to avoid interfering with elastic properties. Also, the important properties of spring rate and percent stretch that are available for heat reactivated elastic materials are less than those available for elastics which are not reactivated with heat.

Diaper elastic members are typically either polymer ribbons or laminates of multiple polymer strands combined with nonwoven sheets. Where an elastic member forms a continuous loop, the elastic member is defined herein as a garter. Elastic members may generally be bonded to substrates in high speed continuous processes by fusion-sealing, heat-activated adhesive sealing, or pressure sensitive adhesive sealing methods. These methods are more generally classified as thermal bonding and adhesive bonding.

Where a garter is stretched circumferentially and bonded to a substrate to create an elasticized opening, it may be necessary to remove substrate material from inside the garter if a hole was not first created in the substrate before bonding. Commercial processes for removing substrate material inside a garter have generally followed the steps of folding the substrate along a machine direction axis passing through the center of the pattern and then cutting out the substrate material inside the pattern by progressively cutting from the folded edge inward and then back to the folded edge. Although progressive cutting can be done at high speeds by rotary knives, by water jet, or by laser, these are all expensive converting processes. Also hole symmetry about the fold axis is generally required since both sides of a hole are cut simultaneously.

Disposable garments having fully elasticized leg openings have the capability of distributing the stretch equally around the leg opening or loop. Fully elasticized leg openings are desired as they provide optimum fit.

It is an object of the present invention to provide a continuous, high-speed method for producing a pant-style garment having fully elasticized leg openings.

It is a further object of the present invention to provide a continuous high-speed method to produce a pant-style garment having a fully elasticized waistband.

It is another object of the present invention to provide a continuous high-speed method to produce a pant-style garment having a reinforced crotch region.

SUMMARY OF THE INVENTION

The present invention provides a continuous, high-speed method for producing a pant-style garment having a pair of fully elasticized leg openings. In a preferred embodiment, a first tensioned elastic ribbon and a second tensioned elastic ribbon are metered tangentially toward a plurality of mandrels. Each mandrel is spaced apart by a gap along a common centerline. Each of the mandrels has a top surface and side walls depending therefrom. The first and second tensioned elastic ribbons are clamped between the mandrels by pushing the first tensioned elastic ribbon toward the common centerline and by pushing the second tensioned elastic ribbon toward the common centerline, thereby encircling the side walls of each of the mandrels as the first and second tensioned elastic ribbons meet at the common centerline. The first and second tensioned elastic ribbons are sealed together where they are clamped in order to form a ribbon seal between each of the mandrels. The first and second tensioned elastic ribbons are cut within the ribbon seal between each of the mandrels so that when cut, the tensioned elastic ribbons form individual tensioned garters about the side walls of each of the plurality of mandrels. Each of the tensioned garters comprises a lower portion that sits about the mandrel side walls and an upper portion that initially sits upward of the mandrel top surface. The upper portion comprises sufficient tension to cause the upper portion of the tensioned garter to fold over onto the top surface of the mandrel to form a garter flange while the lower portion of the tensioned garter clings to the side walls of the mandrel. Next, a substrate or web having two mutually opposed longitudinal edges and a longitudinal centerline is placed adjacent to the garter flange. The substrate is joined or sealed to the garter flange by any suitable sealing means, thereby forming a continuously sealed garter comprising a continuous seal and having an inner edge and an outer edge. A preferable sealing means that forms a continuous seal between the substrate and garter flange is an ultrasonic horn which provides ultrasonic vibration energy to form a fusion-seal or seal between the substrate and garter flange. Preferably, the lower or unbonded portion of the garter is removed and/or severed from the garter flange. The seal between the substrate and the sealed garter is then weakened inboard of the sealed garter inner edge, thereby forming an unsecured substrate portion being substantially inboard of the garter inner edge. The unsecured substrate portion is removed thus forming an aperture around which a remaining portion of the tensioned garter may contract, i.e., the aperture is outlined by a tensioned edge that corresponds to the inner edge of the sealed garter. The apertured substrate is folded along its longitudinal centerline, thereby aligning the two longitudinal edges of the substrate. The folded substrate is now joined or sealed in discrete locations, thereby forming lines of joinder that extend perpendicularly to the longitudinal centerline of the substrate from one longitudinal edge to a tensioned edge of the aperture. Next, the substrate is cut through the line of joinder to form a pant-style garment having a pair of fully elasticized leg openings, a front region, a crotch region and a rear region. When a sealed garter comprising a garter flange is cut, whereby an individualized pant-style garment is formed, two new garters are formed. Additionally, two elasticized leg openings which each comprise a new garter are fully elasticized about their perimeter. That is, each elasticized leg opening comprises a new garter that substantially extends about the perimeter of the leg opening.

In a particularly preferred embodiment, the present invention comprises the additional steps of simultaneously feeding a pair of tensioned elastic ribbons along each longitudinal edge of the substrate or web. As in other known processes, a continuous elastic ribbon may be fed parallel to the direction of substrate web travel or machine direction from a source metering the elastic ribbon at a lower rate of speed than the speed of the substrate web. As the elastic ribbon is progressively bonded to the substrate web in the nip of a pair of sealing rolls, the elastic is stretched between its metering source and the sealing rolls. It is stretched an amount depending on the speed differential between the substrate web and the elastic ribbon metering rolls. Note, elastic ribbons are preferably metered and bonded along each longitudinal edge of the substrate. When the substrate is folded and then joined and cut, a pant-style garment having a fully elasticized waist is formed.

In an alternative embodiment, a substrate that has been sealed to one or more garter flanges is cut substantially inboard of the inner edge of the garter along the perimeter of the inner edge while leaving at least two uncut portions called hinge potions. Also, the substrate that lie within the garter inner edge are cut perpendicularly to the longitudinal centerline from a point inboard of the garter inner edge to an opposite point inboard of the inner edge. From this a pair of crotch potions are formed. Note, the hinge portions are located between the inner edge and the crotch portions. Next, the crotch potions are folded over onto the substrate via the hinge portions. The portion of the substrate onto which the crotch portions are folded will later become the crotch region of the pant-style garment. In this embodiment, the crotch region will preferably comprise two crotch portions that are joined to it to produce a reinforced crotch region.

Another step that can be included in this embodiment provides the step of stripping the tensioned garter from the mandrel while applying vacuum to the portion of the substrate inside the garter from the top surface of the mandrel so that the edge of the continuous seal is broken when the substrate and the remaining portion of the tensioned garter are stripped off the mandrel. The portion of the substrate to be removed is held by vacuum to the top surface of the mandrel until after an aperture is completely formed in the substrate.

BRIEF DESCRIPTION OF DRAWINGS

While the specification concludes with claims which particularly point out and distinctly claim the present invention, it is believed that the present invention will be better understood from the following description of preferred embodiments, taken in conjunction with the accompanying drawings, in which like reference numerals identify identical elements and wherein:

FIG. 2a is a simplified perspective view of a preferred embodiment of the method and apparatus for combining a tensioned elastic garter with a substrate of the present invention, disclosing a garter wrapped about a mandrel;

FIG. 2b is a front elevational view of the embodiment of FIG. 2a, without the garter, showing the angle between mandrel top surface and its depending side walls;

FIG. 3 is a simplified perspective view of the embodiment of FIG. 2a, showing the upper portion of the elastic garter folded over the top surface of the mandrel to form a garter flange;

FIG. 4 is a simplified perspective view of the embodiment of FIG. 3, showing a substrate brought into contact with the garter flange;

FIG. 5 is a simplified perspective view of the embodiment of FIG. 4, showing an ultrasonic horn bonding the substrate to the garter flange;

FIG. 6 is an enlarged partial front elevation section view, taken along section line 6—6 of FIG. 5, showing the interface between ultrasonic horn, substrate, tensioned elastic garter, and mandrel during the step of sealing the garter flange to the substrate and weakening the bond at the edge of the seal;

DETAILED DESCRIPTION OF THE INVENTION

The term "pant-style garment", as used herein refers to a discrete, unitary structure having a front region, a crotch region and a back region whereby the pant-style garment can function as a garment, an outer surface to an absorbent article, or as any type of wearable structure employing the use of fully elasticized leg openings and/or fully elasticized waistbands.

Figure 1:
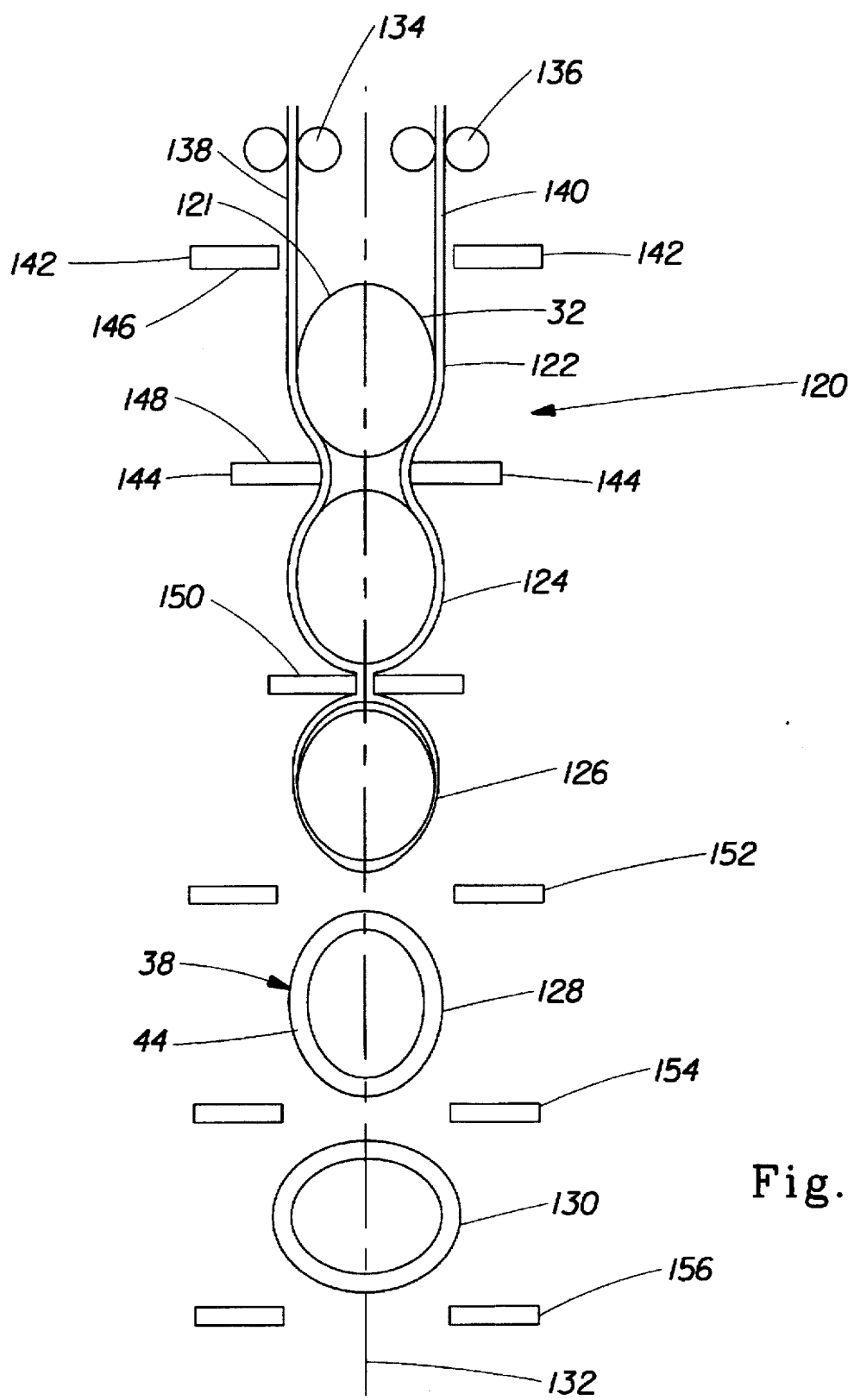
FIG. 1 is a top plan view of five mandrels having garters formed about them in a progressive fashion.

In FIGS. 1–8b and 10a–10b there is shown a preferred embodiment of the present invention, which provides a method and apparatus for forming a fully elasticized pant-style garment in a high-speed, continuous process. In FIG. 1, embodiment 120 provides an apparatus which includes a mandrel 32 shown having a series of five positions, designated 122, 124, 126, 128, and 130, all having a common centerline 132 and with substantially equally spaced gaps between mandrel positions. Mandrel 32 is preferably oval.

FIG. 1 shows two pair of metering rolls 134 and 136 located in a fixed position upstream of mandrel position 122. Metering roll pairs 134 and 136 feed elastic ribbons 138 and 140 respectively, tangentially to mandrel 32. As mandrel 32 is moved from its initial position 122 to position 124, the elastic ribbons 138 and 140 are stretched in a direction substantially parallel to the common centerline 132. Elastic ribbons 138 and 140 may be made as homogeneous sheets of elastic or laminates of elastic strands and nonwovens, or any other continuous webs of material capable of being stretched. Mandrels are either indexed from position to position or they move together at a constant speed.

Moving along with mandrel 32 are clamp pairs 142 and 144. Each clamp of the pair 142 moves perpendicular to common centerline 132 in unison with its mate. Each clamp of the pair 144 moves similarly to those of pair 142 but at a different time in the process. Clamp pair 142 is shown open in position 146 outside the elastic ribbons 138 and 140, and clamp pair 144 is shown closing against the elastic ribbons, thereby pushing them toward common centerline 132 in position 148. When the mandrel 32 reaches position 124, clamp pair 142 moves to position 148 and clamp pair 144 moves to position 150.

As the mandrel 32 moves forward, the clamp pairs close on the elastic ribbons progressively until both ribbons are clamped at common centerline 132, as shown by clamp position 150. When each pair of clamps reach the closed position 150, elastic ribbons 138 and 142 are pressed against each other and sealed together by sealing means within the clamps. Also within each pair of clamps is a means for cutting the ribbon within the sealed region in order to separate the sealed elastic ribbon of one mandrel from that of the adjacent mandrel. A preferred clamp/seal/cut device is disclosed in U.S. Pat. No. 5,393,360 issued to Bridges et al. on Feb. 28, 1995 and is hereby incorporated herein by reference. After remaining closed long enough for ribbon sealing and cutting, the closed clamp pairs open as shown in clamp position 152. Once opened, clamp pairs remain open as shown in subsequent positions 154 and 156.

In the clamp/seal/cut process of apparatus 120, the elastic ribbons 138 and 140 are progressively wrapped around the side walls of a mandrel to form a complete loop. At clamp position 150, the ribbons 138 and 140 are sealed and cut at the leading end of the mandrel in position 124 and at the trailing end of the mandrel in position 126. Thus, at mandrel position 126, a tensioned garter 38 is first formed, and a garter flange 44 is formed by mandrel position 128.

Elastic ribbons 138 and 140 may be metered in a partially contracted state at the speed of mandrel 32 traveling along common centerline 132. In this case the tension eventually applied to the ribbons would be a function of the amount of wrap applied to them around the mandrel 32. The ribbons may also be metered more slowly than the speed of mandrel travel such that stretch occurs during metering. Other tensioning arrangements are within the scope of the present invention as long as the garter has been tensioned some amount when formed around the mandrel.

At mandrel position 130 the oval mandrel is shown rotated 90°. Depending on the product application for the elastic garter, it may be required to have the oval garter oriented differently between the forming process and the downstream substrate securement process. A different mandrel orientation for garter forming may be desirable in order to minimize the amount of stretch imparted to the elastic ribbons as they are wrapped around the mandrel. When the elastic ribbon is metered parallel to the common centerline 132, less stretch is imparted during wrapping if the major axis of the oval is parallel to the common centerline 132 than if the major axis is perpendicular to the common centerline 132. Also, wrapping elastic ribbons around mandrels that are oriented such that there is minimum travel of the wrapping mechanism is important for high speed garter forming. FIG. 1 shows that if mandrel 32 is pivotable about its top surface center, it may be rotated at position 130 in order to meet both the garter forming and securement requirements.

Figure 10A:
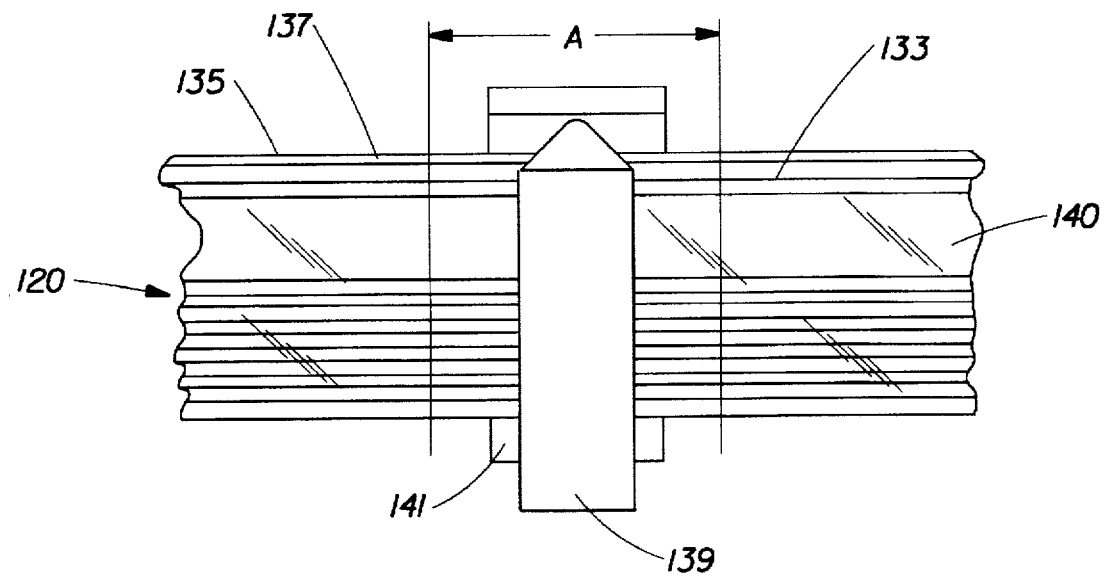
FIG. 10a is a simplified perspective view of an alternative embodiment of the method and apparatus of FIG. 1, showing a tensioned elastic ribbon being compressed between a blunt tool and an anvil surface.
Figure 10B:
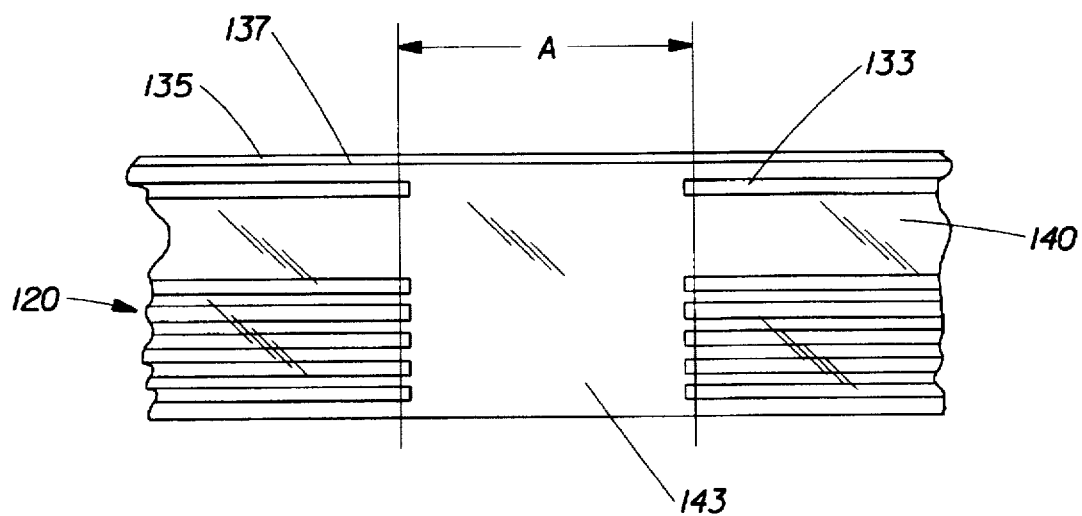
FIG. 10b is a simplified perspective view of the tensioned elastic ribbon of FIG. 10a, showing elastic strands within a small area of the tensioned elastic ribbon having been burst and contracted.

FIGS. 10a and 10b show an alternative for elastic ribbon construction for the embodiment 120. Instead of a uniformly continuous elastic ribbon, the alternative ribbon preferably has unbonded locations which have no elastic in them, equally spaced along the length of each elastic ribbon. Such unbonded locations may be registered with the gaps between mandrels so that the ribbon sealing and cutting operations there do not have to seal and cut through elastic. If the tensioned elastic ribbons are made of a trilaminate of polypropylene nonwoven outer layers 135 and 137 and natural rubber elastic strands 133 bonded therebetween, it is preferable to avoid heat sealing through natural rubber, because the presence of such rubber weakens the seal between the two tensioned elastic ribbons bonded around the mandrels.

A trilaminate 140 made of nonwoven outer layers 135 and 137 and a plurality of natural rubber elastic strands 133 is preferably constructed by applying intermittently an adhesive to the stretched strands 133 when they are combined with the outer layers. In order to provide unbonded locations in the elastic ribbons, having a length A of about 1 to 3 inches (2.5 mm to 7.6 mm) long, in which there are no elastic strands, the laminate 140 is first bonded together with the unbonded locations having no adhesive applied. That is, stretched elastic strands 133 extend through each unbonded location, bonded at each side of the unbonded location but not bonded within it. Following such interrupted bonding, each tensioned elastic ribbon 138 or 140 is exposed to a compression process which bursts the elastic strands passing through each unbonded location. In this process a blunt tool 139 presses against the trilaminate 140 backed by a substantially planar anvil surface 141. A fixed gap between tool 139 and anvil 141 of 0.001 inches (0.0025 mm) generates a localized pressure of 30,000 to 40,000 psi (2041 to 2722 atm.), which is sufficient to burst the plurality of natural rubber strands 133 without cutting the polypropylene nonwoven layers 135 and 137. Once the elastic strands 133 are burst, they contract to the edges of the small area, leaving a small area 143 in which there are no elastic strands passing through it. FIG. 2b shows top surface 34 to be substantially planar and that side walls 36 depend from the top surface 34 at an angle 37. Preferably, the angle 37 is at least 270°.

FIG. 2a shows the completed tensioned elastic garter 38 from FIG. 1 now being wrapped around mandrel 32. Elastic garter 38 has a lower portion 40 and an upper portion 42. Lower portion 40 clings tightly to side walls 36 of mandrel 32 due to the tension in the garter. FIG. 2a shows elastic garter 38 positioned with upper portion 42 above top surface 34 of mandrel 32. In this position, the tension in upper portion 42 of elastic garter 38 causes the upper portion 42 to fold onto top surface 34 in order to relieve some of the tension in upper portion 42, as shown in FIG. 3. Thus, FIG. 3 represents the stable condition of tensioned elastic garter 38 when it is positioned with its upper portion 42 above top surface 34 and its lower portion 40 wrapped around mandrel 32. In this condition upper portion 42 takes the form of an inward facing garter flange 44.

FIG. 4 shows a substrate 54 placed against the garter flange 44. Substrate 54 is shown as transparent for illustration purposes, but it may be made of any material which is securable to the material of garter flange 44. Substrate 54 is preferably a nonwoven web of polypropylene fibers. Other suitable materials for use as the substrate 54 include but am note limited to plastic films, woven webs, other nonwoven webs, laminates and composites thereof. FIG. 4 shows substrate 54 in sheet form, but it may also be a continuous web. Garter 38 is preferably made of two nonwoven polypropylene strips, or one wide strip folded into two halves, which are bonded to multiple strands of elastic sandwiched between them by intermittent glue stripes.

In a preferable embodiment of the sealing step, FIG. 5 shows an ultrasonic sealing horn 56 in contact with substrate 54 and positioned perpendicular to the top surface 34 of mandrel 32. Passing the top surface 34 of mandrel 32 under vibrating ultrasonic horn 56 enables ultrasonic horn 56 to progressively fusion-seal substrate 54 to garter flange 44, using top surface 34 of mandrel 32 as an anvil. Garter flange 44 and substrate 54 remain fixed relative to mandrel top surface 34 during the bonding process. Vibration energy, which melts the interface between substrate 54 and garter flange 44, is delivered by vibrating horn 56 from a source not shown. A fusion-seal 46 between garter flange 44 and substrate 54 is thereby generated. The term "fusion-seal" or "seal" refers to a bond formed between two or more surfaces that is securely joined at the bond site.

FIG. 6 shows the ultrasonic fusion bonding process in more detail. Mandrel 32 may preferably have a substantially planar top surface 34, as shown in FIG. 2b, if sufficient sealing energy can be applied to generate a fusion-seal the width of the garter flange. More preferably, top surface 34 has a raised outer rim 58 which extends above top surface 34. Rim 58 provides a focal point for ultrasonic vibration energy from horn 56 so that a fusion-seal 46 is formed between substrate 54 and garter flange 44 only where rim 58 supports garter flange 44.

An elastic garter may be bonded to a substrate with or without an opening inside the garter flange. It is preferable to have an opening around which the garter may contract. If an opening has been provided in the substrate prior to sealing, registration of the opening to the garter flange is required. More preferably an opening is created after sealing, and as part of the sealing process. Therefore, rim 58 preferably has a peak 60 (shown in FIG. 6) at its upper surface, rising slightly above rim 58. Peak 60 acts to thin the fusion-seal between garter flange 44 and substrate 54. Where seal 46 is so thinned, it is weakened relative to the rest of the fusion-seal. Thus, outer rim 58 has a shape adapted to fusion-seal the garter flange 44 to the substrate 54, but with an edge of the fusion-seal weakened enough that material inside the continuous seal 46 can later be removed by stressing the weakened center enough to break it. Mandrel 32 is shown having a vacuum hole 48 connected to a vacuum source not shown. The purpose of vacuum hole 48 is discussed hereinafter.

Outer rim 58 and peak 60 are preferably continuous around the perimeter of top surface 34 of mandrel 32. If rim 58 were discontinuous, the fusion-seal between garter flange 44 and substrate 54 would also be discontinuous. Having a discontinuous sealing pattern for an elastic garter, combined with a process for cutting the garter between fusion-seals, would enable attaching independently functional, tensioned elastics to a substrate in both machine direction and cross direction with one bonding step. Preferably, after sealing the substrate 54 to the garter flange 44 the lower portion 40 of the garter 38 is removed, most preferably by a cutting means.

Figure 7:
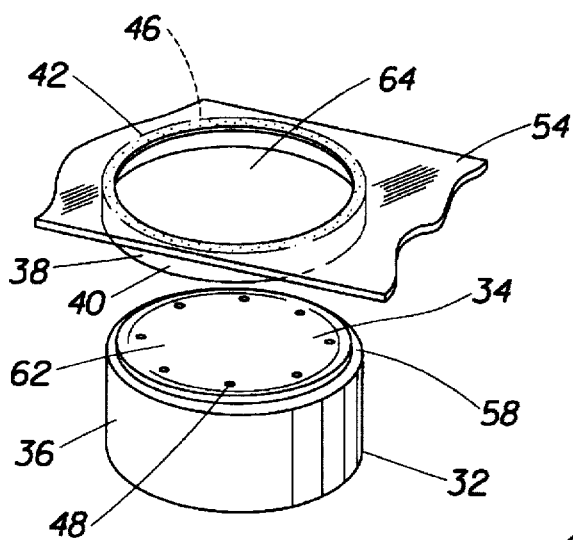
FIG. 7 is a simplified perspective view of the embodiment of FIG. 5, showing the substrate and garter stripped off the mandrel, while a portion of the substrate and a portion of the garter flange inside the garter are held to the mandrel by vacuum.

FIG. 7 shows a segment of the substrate 54 stripped from mandrel 32, carrying tensioned elastic garter 38 with it. The weakened part of fusion-seal 46 at peak 60 (not shown) is weak enough that material 62, i.e., a portion of the substrate and of the garter flange inside the fusion-seal, is easily broken away from the strong part of the fusion-seal if material 62 is held against top surface 34 of mandrel 32 as the substrate 54 is stripped away. Material 62 is preferably held to top surface 34 by a vacuum from holes 48 in top surface 34, the source of which is not shown. By the process of simultaneously stripping the substrate 54 from the mandrel 32 and holding the material 62 to the mandrel, an aperture 64 is created in substrate 54 around which tensioned garter 38 may contract, thereby forming an elasticized opening 69 in substrate 54.

Figure 7A:
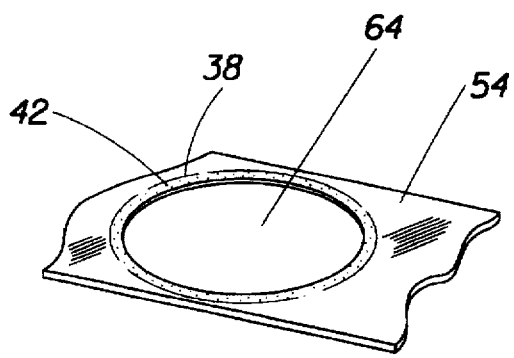
FIG. 7a is a simplified perspective view of the embodiment of FIG. 5, showing the lower portion of the garter having been removed from the garter.

In FIG. 7A, the lower portion 40 (not shown) of the garter 38 has been removed from the garter and substrate 54. The lower portion 40 can be removed by various methods known in the art. One method is to weaken the line of connection between lower portion 40 and upper portion 42. Then, the portions 40 and 42 can be detached by cutting, pulling and/or tearing the portions apart preferably at the line of connection. The term "line of connection" refers to a line, zone or area at which two or more materials, zones portions or segments are connected.

The aforementioned is the preferred method for attaching a tensioned garter to a substrate. However, other suitable methods exist for attaching a tensioned garter to a substrate. For example, U.S. Pat. No. 5,393,360 issued to Bridges et al. on Feb. 28, 1995 discloses several suitable methods for attaching a tensioned garter to a substrate all of which are hereby incorporated herein by reference.

Figure 8:
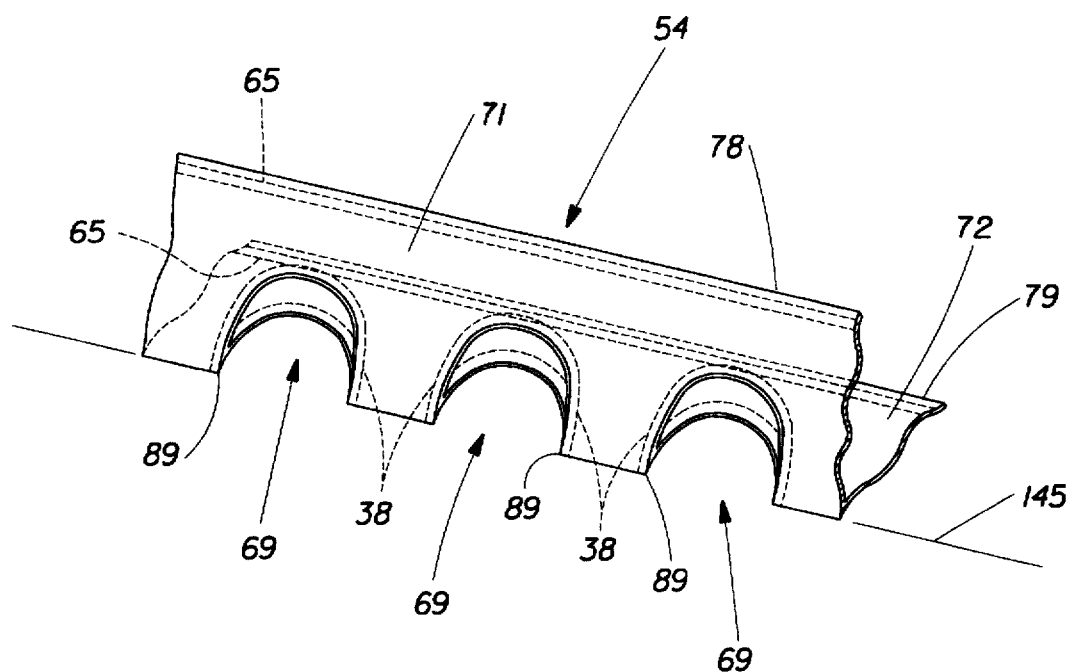
FIG. 8 is a perspective view of the substrate folded along its longitudinal centerline.

FIG. 8 shows the apertured substrate or web 54 having longitudinal edges 78 and 79 and tensioned garters 38 secured thereto, being folded about its longitudinal centerline 145. The substrate 54 has a first or front region 71 on one side of the centerline 145 and a second or back region 72 on the opposite side of the longitudinal centerline 145. In practice, the substrate 54 is preferably folded in half about the longitudinal centerline 145 such that the longitudinal edges 78 and 79 are aligned with one another. The substrate 54 has a plurality of elasticized openings 69 about which tensioned garters 38 extend.

Figure 8A:
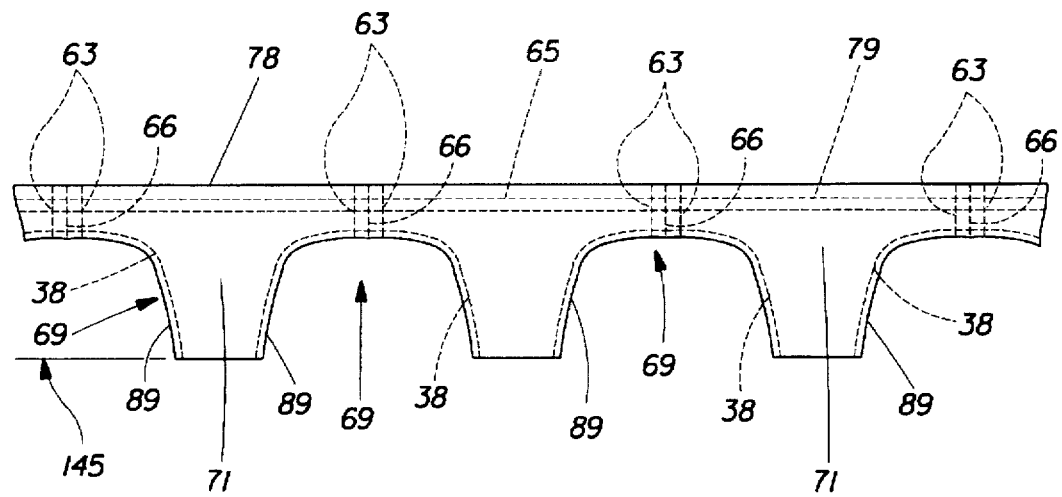
FIG. 8a is a plan view of a series of un-cut pant-style garments that are bonded along their lines of joinder.

FIG. 8a shows portions of the substrate 54 of FIG. 8 being joined together about an area from the longitudinal edges 78 and 79 to an opening edge 89, thus forming lines of joinder 63. By the term "lines of joinder" it is meant herein a line or region about which a side closure is formed by joining the substrate 54 to itself about an area from its longitudinal edges to an edge of opening 69. Cut lines 66 are shown extending through the lines of joinder 63. When the garter 38 is cut (FIG. 8b), whereby an individualized pant-style garment 75 is formed, two new garters 38a are formed from the single garter 30. Additionally, two fully elasticized leg openings 70 are formed from each elasticized openings 69. Each fully elasticized leg opening 70 comprises a new garter 38a that substantially extends about the entire perimeter of the leg opening 70. Thus, from one elasticized opening 69, two fully elasticized openings 70 are produced when the substrate 54 is joined and cut into individualized pant-style garments 75, whereby each new garter 38a serves to fully elasticize each leg opening 70 of pant-style garment 75.

Figure 8B:
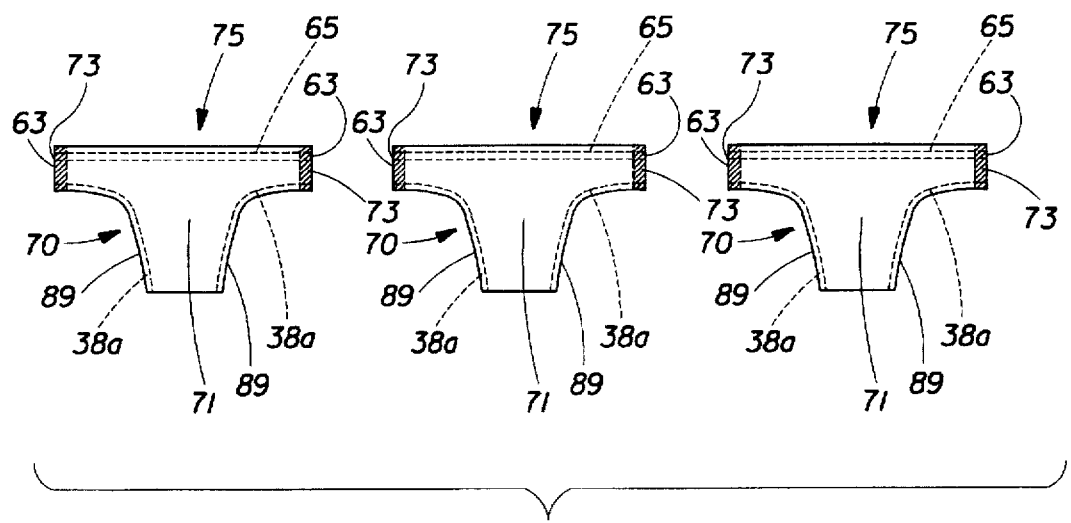
FIG. 8b is a plan view of the pant-style garments in FIG. 8a that have been detached from one-another.

In forming the pant-style garment 75 (FIGS. 8a and 8b), the substrate 54 will be joined or sealed in discrete locations, thereby forming lines of joinder 63 and then cut through the lines of joinder 63 along cut lines 66 to form individual pant-style garments 75 having fully elasticized leg openings 70. The front region 71 and the back region 72 may be joined together along lines of joinder 63 using any suitable method. Examples of suitable methods for joining the back region and the first region together include but are not limited to a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The method can comprise an open pattern network of filaments of adhesive as is disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, and ultrasonic bonds. FIG. 8b provides a view of detached, individual pant-style garments 75 that have been disconnected. The folded substrate 54 shown in FIG. 8a is cut through lines 66 to form detached, individual pant-style garments 75. The folded substrate 54 is preferably cut through the line of joinder 63 to form side seams 73 in the pant-style garments 75.

In a particularly preferred embodiment, the present invention comprises the additional steps of simultaneously feeding a pair of tensioned elastic ribbons along each longitudinal edge 78, 79 of the substrate or web. As in other known processes, a continuous elastic ribbon may be fed parallel to the direction of substrate web travel or machine direction from a source metering the elastic ribbon at a lower rate of speed than the speed of the substrate web. As the elastic ribbon is progressively bonded to the substrate web in the nip of a pair of sealing rolls, the elastic is stretched between its metering source and the sealing rolls. It is stretched an amount depending on the speed differential between the substrate web and the elastic ribbon metering rolls. Note, elastic ribbons are preferably metered and bonded along each longitudinal edge of the substrate as shown in FIGS. 8–8b. Thus, when the substrate is folded and then joined and cut, a pant-style garment having a fully elasticized waist is formed.

Figure 9:
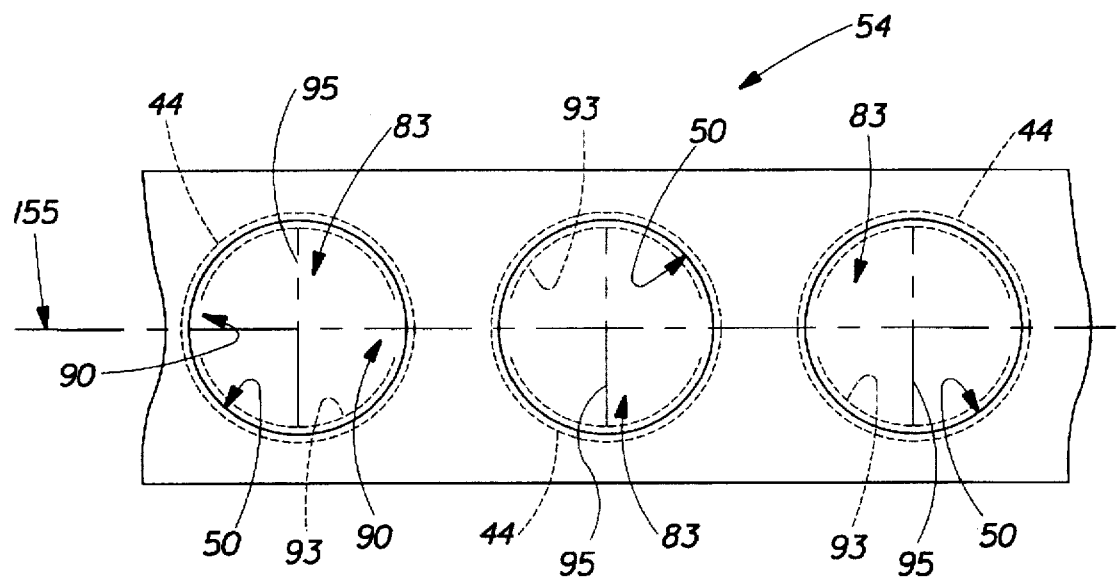
FIG. 9 is a plan view of an alternative embodiment that provides a reinforced crotch region in a formed pant-style garment.
Figure 9A:
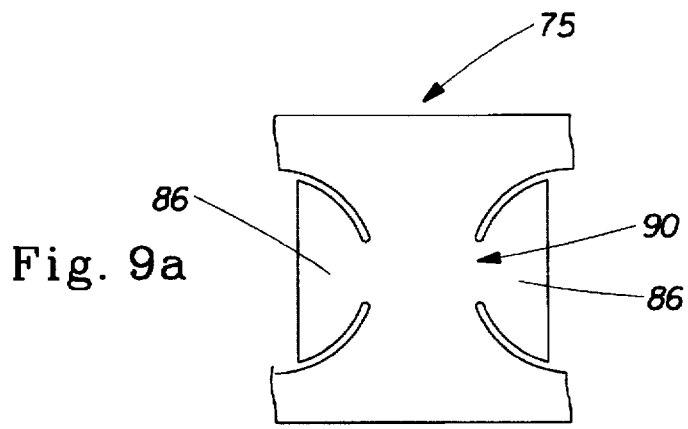
FIG. 9a is a plan view of a cut portion from the substrate in FIG. 9 that shows unfolded portions of the substrate to be used in the reinforced crotch region.
Figure 9B:
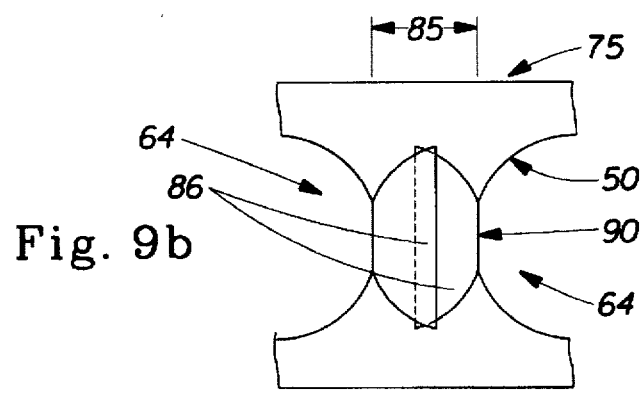
FIG. 9b is a plan view of the embodiment in FIG. 9a that shows the folded portions of the substrate in the reinforced crotch region.

In an alternative embodiment, the pant-style garment 75 can comprise a reinforced crotch region 85. FIG. 9 shows a substrate 54 that has been provided with elasticized garter flanges 44 that have been sealed to the substrate 54. The inner portion 83 of the substrate within the garter flanges 44 is cut substantially inboard along the perimeter of the inner edge 50 of the sealed garter 38 (not shown) along cut line 93 while leaving at least two portions uncut that are called hinge portions 90. Also, this inner portion 83 is cut perpendicularly with respect to the longitudinal centerline 155 from a point across the longitudinal centerline 155 and inboard of said sealed garter inner edge 50 to an opposite point inboard of the inner edge 50 along line 95, thereby forming a pair of crotch portions 86. FIG. 9a shows a portion of substrate 54 of FIG. 9 in which crotch portions 86 have been cut and formed and now await to be folded to form a reinforced crotch region 85 of the pant-style garment 75. FIG. 9b discloses the pant-style garment 75 of FIG. 9a in which the crotch portions 86 have been folded over onto the substrate 54 to form a reinforced crotch region 85. Note, the hinge portions 90 are between the inner edge 50 and the now formed crotch portions 86. Next, the crotch potions 86 are folded over onto the substrate 54 via the hinge portions 90, to form a reinforced crotch region 85 in the pant-style garment 75. As the crotch portions 86 are folded over onto the substrate 54, fully elasticized leg openings 70 within the seal inner edges 50 are simultaneously formed. The folded crotch portions 86 are preferably sealed to the substrate 54, thereby forming a sealed, reinforced crotch region 85. After the formation of the reinforced crotch region 85, the substrate 54 is then folded, joined in the manner previously disclosed herein and cut to form discrete pant-style garments 75.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A continuous, high-speed method for producing a pant-style garment having a pair of fully elasticized leg openings, said method comprising the steps of:

a) metering a first tensioned elastic ribbon and a second tensioned elastic ribbon tangentially toward a plurality of mandrels, each of said mandrels being spaced apart by a gap along a common centerline and having a top surface and side walls depending therefrom whereby at least a portion of each of said tensioned elastic ribbons projects above said uppermost surface of said mandrels;

b) clamping said first and second tensioned elastic ribbons between each of said plurality of mandrels by pushing said first tensioned elastic ribbon toward said common centerline and by pushing said second tensioned elastic ribbon toward said common centerline, thereby encircling said side walls of each of said mandrels, as said first and second tensioned elastic ribbons meet at said common centerline;

c) sealing said first and second tensioned elastic ribbons where they are clamped together in order to form a ribbon seal between each of said plurality of mandrels;

d) cutting said first and second tensioned elastic ribbons within said ribbon seal between each of said plurality of mandrels so that when cut, said tensioned elastic ribbons form individual tensioned garters about said side walls of said plurality of mandrels, each said tensioned garter having an upper portion being upward of said mandrel top surface and a lower portion, said upper portion of said tensioned garter having sufficient tension to cause said upper portion of said tensioned garter to fold over onto said top surface of said mandrel to form a garter flange while said lower portion of said tensioned garter clings to said side walls of said mandrel;

e) placing a substrate having two mutually opposed longitudinal edges, and a longitudinal centerline adjacent to said garter flange;

f) sealing said substrate to said garter flange thereby forming a continuously sealed garter comprising a continuous seal, said sealed garter having an inner edge and an outer edge;

g) cutting said substrate substantially inboard of said inner edge along the perimeter of said inner edge while leaving at least two uncut portions, thereby forming hinge portions and also cutting perpendicularly to said longitudinal centerline from a point inboard of said inner edge to an opposite point across said longitudinal centerline and inboard of said inner edge, thereby forming a pair of crotch portions, said hinge portions being between said inner edge and said crotch portions;

h) folding said crotch portions over onto said substrate by said hinge portions, thereby forming apertures in said substrate;

i) folding said substrate along said longitudinal centerline thereby aligning said longitudinal edges of said substrate;

j) joining said folded substrate along a line of joinder in a direction perpendicular to said longitudinal centerline, said line of joinder being from said longitudinal edge to said tensioned edge of said aperture; and k) cutting said substrate through said line of joinder to form a discrete pant-style garment having a pair of fully elasticized leg openings, each said garment having a front region, a crotch region and a back region.

2. The method of claim 1 further comprising the step of sealing said crotch portions to said crotch region of said pant-style garment to form a secured crotch region.

* * * * *

UNITED STATES PATENT AND TRADEMARK OFFICE
CERTIFICATE OF CORRECTION

PATENT NO. : 5,733,401
DATED : March 31, 1998
INVENTOR(S) : E. Kelly Linman et al.

It is certified that error appears in the above-identified patent and that said Letters Patent is hereby corrected as shown below:

<u>Title page, Item [57],</u>
Line 6, of the Abstract, "fired" should read -- fitted --.

<u>Column 4,</u>
Line 7, "potion" should read -- portions --.
Line 7, "He" should read -- lie --.
Line 11, "potion" should read -- portions --.
Line 15, "potion" should read -- portions --.

<u>Column 7,</u>
Line 55, "am note" should read -- are not --.

<u>Column 11,</u>
Line 9, "wails" should read -- walls --.
Line 36, "wails" should read -- walls --.

Signed and Sealed this

Sixteenth Day of October, 2001

Attest:

NICHOLAS P. GODICI
*Attesting Officer*   *Acting Director of the United States Patent and Trademark Office*